US006699666B1

(12) United States Patent
Homma et al.

(10) Patent No.: US 6,699,666 B1
(45) Date of Patent: Mar. 2, 2004

(54) METHOD FOR THE DIAGNOSIS OF CELL PROLIFERATIVE DISEASE

(75) Inventors: Yoshimi Homma, Fukushima (JP); Noritaka Oyama, Fukushima (JP); Koichiro Sato, Fukushima (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/787,292

(22) PCT Filed: Sep. 17, 1999

(86) PCT No.: PCT/JP99/05069

§ 371 (c)(1),
(2), (4) Date: Mar. 15, 2001

(87) PCT Pub. No.: WO00/17339

PCT Pub. Date: Mar. 30, 2000

(30) Foreign Application Priority Data

Sep. 18, 1998 (JP) ............................................ 10-265089

(51) Int. Cl.[7] ............................ C07H 21/04; C12Q 1/68
(52) U.S. Cl. ........................ 435/6; 435/91.2; 435/91.1; 536/23.1; 536/24.3
(58) Field of Search ........................ 435/6, 91.2, 91.1; 536/23.1, 24.3, 24.1, 24.33, 25.3; 436/97

(56) References Cited

FOREIGN PATENT DOCUMENTS

| WO | WO 97/44456 | 11/1997 |
| WO | WO 98/00552 | 1/1998 |
| WO | WO 98/40487 | 9/1998 |
| WO | WO 99/07854 | 2/1999 |

OTHER PUBLICATIONS

Gamou, et al., Japanese Journal of Cancer Research 79:989–995, 1988.*
Johnson, et al., The Journal of Biological Chemistry 263(12):5693–5699, 1988.*
Kaneko, et al., Japanese Journal of Cancer Research 76:1136–1140, 1985.*
Ishii, et al. Proceedings of the National Academy of Sciences of the United States of America 82:4920–4924, 1985.*
Holzmann, et al., Anticancer Research 12:1013–1018, 1992.*
Sambrook, Fritsch, Maniatis, Molecular Cloning, A Laboratory Manual, 2nd edition, vol. 1, Cold Spring Harbor Press, 1989, New York.
Sambrook, Fritsch, Maniatis, Molecular Cloning, A Laboratory Manual, 2nd edition, vol. 2, Cold Spring Harbor Press, 1989, New York.
Sambrook, Fritsch, Maniatis, Molecular Cloning, A Laboratory Manual, 2nd edition, vol. 3, Cold Spring Harbor Press, 1989, New York.

Kaneko Y et al., "Hypomethylation of C–Myc and Epidermal Growth Factor Receptor Genes in Human Hepatocellular Carcinomas and Fetal Liver", Japanese Journal of Cancer Research, vol. 76, No. 12, 1985, pps. 1136–1140.
Human Molecular Genetics vol. 2, No. 7 (1993), Annett Behn–Krappa et al., "The state of DNA methylation in the promoter and exon 1 regions of the human gene for the interleukin–2 receptor α chain (IL–2R α) in various cell types", pp. 993–999.
Cell, vol. 70, (1992), Adrian Bird, "The Essentials of DNA Methylation", pp. 5–8.
Blood, vol. 93, No. 12, (1999), Rakesh Singal et al., "DNA Methylation", pp. 4059–4070.
BioEssays, vol. 17, No. 2, (1995), Roger L. P. Adams, "Eukaryotic DNA methyltransferases–structure and function", pp. 139–145.
Proc. Natl. Acad. Sci. USA, vol. 96, (1999), Alan P. Wolffe et al., "DNA demethylation", pp. 5894–5896.
Trend in Genet. (TIG), vol. 13, No. 8, (1997), Rudolf Jaenisch, "DNA methylation and imprinting: why bother?", pp. 323–329.
Trend in Genet. (TIG), vol. 13, No. 11, (1997), Stefan U. Kass et al., "How does DNA methylation repress transcriptions?", pp. 444–449.
Nature, vol. 389, (1997,) Anton Wutz et al., "Imprinted expression of the Igf2r gene depends on an intronic CpG island", pp. 745–749.
J. Biochem, vol. 125, No. 2, (1999), Tapas K. Kundu et al., "CpG Islands in Chromatin Organization and Gene Expression", pp. 217–222.
Adv. Cancer Res., vol. 72, (1998), Stephen B. Baylin et al., "Alterations in DNA Methylation: A Fundamental Aspect of Neoplasia", pp. 141–196.
Nucleic Acids Res., vol. 26, No. 10, (1998,) Theo Rein et al., "Identifying 5–methylcytosine and related modifications in DNA genomes", pp. 2255–2264.
Proc. Natl. Acad. Sci. USA, vol. 96, (1999), Masahiko Shiraishi et al., "Isolation of DNA fragments associated with methylated CpG islands in human adenocarcinomas of the lung using a methylated DNA binding column and denaturing gradient gel electrophoresis", pp. 2913–2918.
Proc. Natl. Acad. Sci. USA, vol. 89, (1992) Marianne Frommer et al., "A genomic sequencing protocol that yields a positive display of 5–methylcytosine residues in individual DNA strands" pp. 1827–1831.

(List continued on next page.)

Primary Examiner—Jehanne Souaya
Assistant Examiner—Jeanine Goldberg
(74) Attorney, Agent, or Firm—Venable LLP; Robert Kinberg

(57) ABSTRACT

This invention relates to a diagnostic method for detecting cell-proliferating diseases characterized by analysis of the methylation level of cytosine residues in the region involved in the expression of cytokine receptor gene.

3 Claims, 2 Drawing Sheets

OTHER PUBLICATIONS

*Nucl. Acids Res.*, vol. 22, No. 15, (1994), Susan J. Clark et al., "High sensitivity mapping of methylated cytosines", pp. 2990–2997.

*The Lancet*, vol. 350, (1997), Robert S. Stem, "Psoriasis", pp. 349–353.

*The Lancet*, vol. 338, (1991), Jonathan N. W. N. Barker, "The pathophysiology of psoriasis", pp. 227–230.

*The Lancet*, vol. 338, (1991), Alan Menter et al., "Psoriasis in practice", pp. 231–234.

*Nature Getetics*, vol. 14, (1996), Deborah Matthews et al., "Evidence that a locus for familial psoriasis maps to chromosome 4q", pp. 231–233.

*Science*, vol. 264, (1994), James Tomfohrde et al., "Gene for Familial Psoriasis Susceptibility Mapped to the Distal End of Human Chromosome 17q", pp. 1141–1145.

*Arch. Dermatol.*, vol. 130, (1994), James T. Elder et al. "The Genetics of Psoriasis", pp. 216–224.

*J. Dermatol. Sci.*, vol. 16, (1998), Noritaka Oyama et al., "Different growth properties in response to epidermal growth factor and interleukin–6 of primary keratinocytes derived from normal and psoriatic lesional skin", pp. 120–128.

*J.Biol. Chem.*, vol. 266, (1991), John D. Haley et al., "Contributory Effects of de Novo Transcription and Premature Transcript Termination in the Regulation of Human Epidermal Growth Factor Receptor Proto–oncogene RNA Synthesis", pp. 1746–1753.

*J. Biol. Chem.*, vol. 263, No. 12, (1988), Alfred C. Johnson et al., "Epidermal Growth Factor Receptor Gene Promoter", pp. 5693–5699.

*Dermatologica*, vol. 157, (1978), T. Fredriksson et al., "Severe Psoriasis–Oral Therapy with a New Retinoid", pp. 238–244.

*J. Dermatol. Sci.*, vol. 16, (1998), Junichi Sugai et al., "New method for determining prognosis of patients with psoriasis (E–PAP)", pp. 165–169.

*Nippon Rinsho*, Vol 57, (1999), Tsuyoshi Sakane, "The most recent advance in clinical investigation of rheumatoid arthritis" pp. 333–338, Abstract only; Text not in English.

*Seminars in Arthritis & Rheumatism*, vol. 21, No. 5, (1992), William V. Williams et al., "Tyrosine Kinase Signal Transduction in Rheumatoid Synovitis", pp. 317–329.

*Mol. Cell. Biol.*, vol. 7, (1987), Michael Tal et al., "Human HER2 (neu) Promoter: Evidence for Multiple Mechanisms for Transcriptional Initiation", pp. 2597–2601.

*Proc. Natl. Acad. Sci. USA*, vol. 84, (1987), Shunsuke Ishii et al., "Characterization of the promoter region of the human c–erbB–2 protooncogene", pp. 4374–4378.

*J. Biol. Chem.*, vol. 265, No. 8, (1990), Laurie G. Hudson et al., "Structure and Inducible Regulation of the Human c–erb B2/neu Promoter", pp. 4389–4393.

*Gene*, vol. 136, (1993), Adrienne P. Ertl et al., "Structural features of the 5' region of the human erbB–2 gene", pp. 361–364.

*Cancer Res.*, vol. 54, (1994), Madeleine Grooteclaes et al., "The 6–Kilobase c–erbB2 Promoter Contains Positive and Negative Regulatory Elements Functional in Human Mammary Cell Lines 1", pp. 4193–4199.

*Arthritis Reum.*, vol. 31, No. 3, (1988), Frank C. Arnett et al., "The American Rheumatism Association 1987 Revised Criteria For The Classification Rheumatoid Arthritis", pp. 315–324.

*Biochim. Biophys. Acta.*, vol. 1377, (1998), Eldad Tzahar et al., "The ErbB–2/HER2 oncogenic receptor of adenocarcinomas: from orphanhood to multiple stromal ligands", pp. M25–M37.

*Biochim. Biophys. Acta.*, vol. 1198, (1994), Nancy E. Hynes et al., "The biology of erbB–s/neu/HER–2 and its role in cancer", pp. 165–184.

*J. Biol. Chem.*, vol. 269, (1994), Lena Claesson–Welsh, "Platelet–derived Growth Factor Receptor Signals", pp. 32023–32026.

*Oncogene*, vol. 10, (1995), GB Afink et al., "Molecular cloning and functional characterization of the human platelet–derived growth factor α receptor gene promoter", pp. 1667–1672.

*J. Biol. Chem..*, vol. 270, No. 46, (1995), Kaoru Morishita et al., "A Novel Promoter for Vascular Endothelial Growth Factor Receptor (flt–1) That Confers Endothelial–specific Gene Expression", pp. 27948–27953.

*Proc. Natl. Acad. Sci. USA* vol. 74, No. 3, Louis M. Kunkel et al., "Analysis of human Y–chromosome–specific reiterated DNA in chromosome variants", pp. 1245–1249.

S.L. Beaucage & M.H. Caruthers, *Tetrahedron Letters*, vol. 22, (1981), S.L. Beaucage et al., "Deoxynucleoside Phosphoramidites—A New Class Of Key Intermediates For Deoxypolynucleotide Synthesis", pp. 1859–1862.

\* cited by examiner

FIG. 1

Healthy people

| | -446 | -443 | -427 | -417 |
|---|---|---|---|---|
| N1 | ● | ● | ● | ● |
| N2 | ● | | ● | ● |
| N3 | ● | ● | ● | ● |
| N4 | ● | ● | ● | ● |
| N5 | ● | ● | ● | ● |
| N6 | ● | ● | | ● |
| N7 | ● | ● | ● | |
| N8 | ● | ● | | ● |
| N9 | | ● | ● | ● |
| N10 | ● | ● | ● | ● |
| N11 | ● | ● | | |
| N12 | ● | ● | | |
| N13 | | ● | ● | ● |
| N14 | ● | ● | ● | ● |
| N15 | | ● | | ● |
| N16 | ● | ● | ● | ● |
| N17 | ● | ● | ● | ● |
| N18 | | ● | ● | ● |
| N19 | | ● | ● | ● |
| N20 | ● | ● | ● | |
| N21 | ● | ● | ● | ● |
| N22 | | ● | ● | ● |
| N23 | | ● | ● | ● |
| N24 | | ● | ● | ● |
| N25 | ● | ● | ● | |
| N26 | ● | ● | | ● |
| N27 | | ● | ● | ● |
| N28 | ● | ● | ● | ● |
| N29 | ● | ● | | ● |
| N30 | | | | |

Patients of psoriasis

| | -446 | -443 | -427 | -417 |
|---|---|---|---|---|
| P1 | | ● | | |
| P2 | | | | |
| P3 | | | ● | ● |
| P4 | | | | |
| P5 | | | | |
| P6 | | | | |
| P7 | | ● | | |
| P8 | | ● | ● | ● |
| P9 | | | | |
| P10 | ● | ● | | |
| P11 | ● | | | |
| P12 | | | | |
| P13 | | ● | ● | ● |
| P14 | | | | |
| P15 | | | | |
| P16 | | | | |
| P17 | ● | | ● | ● |
| P18 | | | | ● |
| P19 | | | | |
| P20 | | ● | ● | ● |
| P21 | | | | |
| P22 | | | | |
| P23 | ● | ● | | |
| P24 | | ● | | |
| P25 | | | | |
| P26 | ● | | ● | ● |
| P27 | | | | |
| P28 | | ● | | |
| P29 | | | | ● |
| P30 | | | | |

FIG. 2

Healthy people

|    | -380 | -372 | -360 |
|----|------|------|------|
| C1 | ●    |      | ●    |
| C2 | ●    |      |      |
| C3 | ●    | ●    |      |

Patients of chronic rheumatoid arthritis

|    | -380 | -372 | -360 |
|----|------|------|------|
| R1 | ●    |      |      |
| R2 |      |      |      |
| R3 |      |      |      |
| R4 | ●    |      |      |
| R5 |      |      |      |
| R6 |      |      |      |
| R7 |      |      |      |
| R8 |      |      |      |
| R9 | ●    |      |      |

SEQUENCE LISTING

<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
ccaaaacgaa ttcaaaactc caaccacctc                                      30

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
taggggaagc ttggggattt gaataaagga gt                                   32

<210> SEQ ID NO 3
<211> LENGTH: 582
<212> TYPE: DNA
<213> ORGANISM: Human

<400> SEQUENCE: 3 taggggagg ttggggattt gaataaagga gtagtttttt tgttggtgtt attatttgat     60
gttggtttta aggtttggtt agtttgttta aagttggtat aagtttgttt tgtaaaataa    120
aagaagggaa aggggaagg ggattttggt atagatttgg tttgatttgg atataggttg    180
ggttgtaagt ttgtgggat tgggtttaga ggggtagtgt tgggaatgtt ttttttggaa    240
attaattttt tagggtattg tttttttttt atgtgttgtt ttattttttgt tggagattag   300 gttttgtggg ggttattgtg tttattgttt tgtggttgtt ggttttgggt ttttgttgtt   360 ggttttttttt ttttttttttt gtatttttttt ttttttttgt tttttttgat ttttttttttg   420

```
ttgtttggtt ttttttttt ttgttttgtt ttttgtgttt tggtttgtgt gagttagatg    480
tttgggtagt ttttggtgta gtgtggttgt agtagttttt ttttttttgta tggtgtgagt    540 gtttgttgtg ttgaggtggt tggagttttg agttagtttt gt                       582
```

```
<210> SEQ ID NO 4
<211> LENGTH: 1200
<212> TYPE: DNA
<213> ORGANISM: Human

<400> SEQUENCE: 4
aagcttccgc gagtttccca ggcatttctc ctcgcgggac taccaggggt agtgggacac     60
ttagcctctc taaaagcacc tccacggctg tttgtgtcaa gcctttattc caagagcttc    120
acttttgcga agtaatgtgc ttcacacatt ggcttcaaag tacccatggc tggttgcaat    180
aaacattaag gaggcctgtc tctgcacccg gagttggtgc cctcatttca gatgatttcg    240
agggtgcttg acaagatctg aaggaccctc ggactttaga gcaccacctc ggaacgcctg    300
gcacccctgc cgcgcgggca cggcgacctc ctcagctgcc aggccagcct ctgatccccg    360 cgagggtcc cgtagtgctg caggggagg ctggggaccc gaataaagga gcagtttccc     420
cgtcggtgcc attatccgac gctggctcta aggctcggcc agtctgtcta aagctggtac    480
aagtttgctt tgtaaaacaa agaagggaa aggggaagg ggaccctggc acagatttgg     540
ctcgacctgg acataggctg ggctgcaagt ccgcggggac cgggtccaga ggggcagtgc    600
tgggaacgcc cctctcggaa attaactcct cagggcaccg ctcccctccc atgcgccgcc    660
ccactcccgc cggagactag gtcccgcggg ggccaccgtg tccaccgcct cgcggccgct    720
ggccttgggt ccccgctgct ggttctcctc cctcctcctc gcattctcct cctcctctgc    780
tcctcccgat ccctcctccg ccgcctggtc cctcctcctc ccgccctgcc tccgcgcct    840 cggcccgcgc gagctagacg tccgggcagc cccggcgca gcgcggccgc agcagcctcc    900 tcccccgca cggtgtgagc gcccgccgcg ccgaggcggc cggagtcccg agctagcccc    960
gcggccgccg ccgcccagac cggacgacag gccacctcgt cgcgtccgcc cgagtccccg   1020
cctcgccgcc aacgccacaa ccaccgcgca cggcccctg actccgtcca gtattgatcg   1080
ggagagccgg agcgagctct cggggagca gcgatgcgac cctccgggac ggccggggca   1140
gcgctcctgg cgctgctggc tgcgctctgc ccggcgagtc gggctctgga ggaaaagaaa   1200
```

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
ggtttgggat ggagtaggat gtaag                                            25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
cttatacttc ctcaaacaac cctcc                                            25
```

```
<210> SEQ ID NO 7
<211> LENGTH: 363
<212> TYPE: DNA
<213> ORGANISM: Human

<400> SEQUENCE: 7
ggtttgggat ggagtaggat gtaagttttt taggaagtta gataattgag atttaaaggg      60
tgttaagagt ggtagtttag ggaaatttat tttggatttt ggggagggg gtagagttat     120 tagtttttgt atttagggat tttttgagga aaagtgtgag aatggttgta ggtaatttag     180
gtgttttggt gttaggaggg atgatttagg tttgtgtgaa gagagggaga aagtgaagtt     240
gggagttgtt gatttttaga ttttgttgga atgtagttgg aggggtgag ttgggagtgt     300 gtttgttttt aattattgga gaaggaggag gtggaggagg agggttgttt gaggaagtat     360
aag                                                                  363

<210> SEQ ID NO 8
<211> LENGTH: 647
<212> TYPE: DNA
<213> ORGANISM: Human

<400> SEQUENCE: 8
aggtaaacac aacacatccc cctccttgac tatcaatttt actagaggat gtggtgggaa      60
aaccattatt tgatattaaa acaataggct tgggatggag taggatgcaa gctccccagg     120
aagttagata actgagactt aaagggtgtt aagagtggca gcctagggaa atttatcccg     180
gactccgggg gaggggcag agtcaccagc ctctgcattt agggattctc cgaggaaaag     240
tgtgagaacg gctgcaggca acccaggcgt cccggcgcta ggagggacga cccaggcctg     300
cgcgaagaga gggagaaagt gaagctggga gttgccgact cccagacttc gttggaatgc     360
agttggaggg ggcgagctgg gagcgcgctt gctcccaatc accggagaag gaggaggtgg     420
aggaggaggg ctgcttgagg aagtataaga atgaagttgt gaagctgaga ttcccctcca     480
ttgggaccgg agaaaccagg ggagccccc gggcagccgc gcgccccttc ccacgggcc     540 ctttactgcg ccgcgcgccc ggcccccacc cctcgcagca ccccgcgccc cgcgccctcc     600
cagccgggtc cagccggagc catggggccg gagccgcagt gagcacc                  647
```

METHOD FOR THE DIAGNOSIS OF CELL PROLIFERATIVE DISEASE

This application is a §371 of PCT application PCT/JP99/05069, filed Sep. 17, 1999, and claims priority to Japanese application no. 10-265089, filed Sep. 18, 1998.

TECHNICAL FIELD

This invention relates to a diagnostic method for detecting cell-proliferating diseases characterized by analyzing the methylation level of cytosine residues in the region involved in the expression of cytokine receptor gene.

BACKGROUND ART

DNA of eukaryotes happens to be methylated at cytosine residue of $5^{th}$ position [Cell, 70, 5–8 (1992), Blood, 93, 4059–4070 (1999)]. It is known that the state of methylation of genome DNA of mammalians varies with differentiation or canceration of cells. Methylation reaction is catalyzed by enzymes, DNA(cytosine-5)methyltransferase (EC 2.1.1.37) [BioEssays, 17, 139–145 (1995)]. The enzyme methylates cytosine residue of dinucleotide sequence CpG or trinucleotide sequence CpNpG [N can be anyone of A (adenine), C (cytosine), G (guanine) and T (thymine)]. Furthermore, recognizing specifically the state where only one strand of double strand is methylated, the enzyme methylates cytosine residue in the complementary chain. Recently the existence of an enzyme catalyzing de-methylation of DNA was suggested [Proc. Natl. Acad. Sci. USA, 96, 5894–5896 (1999)]. It is known that the state of methylation of DNA happens to be transmitted to progeny through reproduction (meiosis) by a mode of inheritance called imprinting [Trend in Genet. (TIG), 13, 323–329 (1997)].

Non-coding regions of some genes have a part called CpG island with an abundance of CpG sequence. The state of methylation of cytosine residue in CpG island affects the transcription/expression of the gene. Namely the less methylation results in the accelerated transcription of the gene and the more methylation results in the suppressed transcription [Trends in Genet., 13, 444–449 (1997)]. CpG island affecting gene expression frequently resides in the promoter region of the gene but a case was reported where it resided in the intron [Nature, 389, 745–749 (1997)]. As for the mechanism that DNA methylation in CpG island results in suppressed gene expression, the followings are known. Methylated CpG island is combined with a protein called MeCP2(methyl CpG binding repressor 2) and activates de-acetylation enzyme of histone. As a result neighboring chromatin structure changes into condensed form, which prohibits RNA polymerase or transcription factor from entering into promoter region, and, as a result, the transcription/expression is suppressed [J. Biochem., 125, 217–222 (1999)].

Among cell-proliferating diseases it is known that DNA methylation is involved in cancer development [Adv. Cancer Res., 72, 141–196 (1998)]. However most of the reports advocate that CpG island of a cancer suppression gene is methylated, the expression is lowered and, as a result, cells become cancerous. There has been no report that methylation of cytokine receptor gene is involved. It was also not known with cell-proliferating diseases other than cancers that methylation pattern of genome DNA is changed.

Methods to analyze the state of methylation of genome DNA are known, for example, a method using methylation sensitive restriction enzymes, a method using chemical modification by hydrazine, permanganic acids or sodium bisulfite, an immunological method using antibodies specific to methylated DNA [Nucleic Acids Res., 26, 225–2264 (1998)], and affinity column chromatography method using MBD (methyl-CpG binding domain) like MeCP2 and DGGE (denaturing gradient gel electrophoresis) method [Proc. Natl. Acad. Sci. USA, 96, 2913–2918 (1999)]. Among them the method using sodium bisulfite has been widely used [Proc. Natl. Acad. Sci. USA, 89, 1827–1831 (1992), Nucl. Acids Res., 22, 2990–2997 (1994)].

The method is based on the following principle.

When single strand DNA produced by alkali denaturation is treated by sodium bisulfite, cytosine residues are changed into uracil residues by deamination, while methylated cytosine residues remain intact. Then polymerase chain reaction (hereinafter "PCR") is performed using thus treated DNA as template. The primer therefor is designed to correspond to the base sequence wherein cytosines in base sequence to be amplified are replaced by thymines. When amplification is performed using such primers, methylated cytosine residues in the original genome DNA are amplified as cytosines, while unmethylated cytosine residues are amplified as thymine residues. Thus methylation in the original genome DNA is detected by determining the base sequence of the PCR product.

Psoriasis is a chronic inflammatory skin disease and a cell-proliferating disease accompanying abnormal proliferation of epidermal cells. More than 2% of caucasian population contract it [The Lancet, 350, 349–353 (1997), The Lancet, 338, 227–230 (1991), The Lancet, 338, 231–234 (1991)]. They get it after becoming adult in most cases. The cause of psoriasis is yet to be solved. Although families with high incidence of psoriasis are known and there are reports suggesting the involvement of genetic factor, the cause itself is not yet known [Nature Getetics, 14, 231–233 (1996), Science, 264, 1141–1145 (1994), Arch. Dermatol., 130, 216–224 (1994)]. On the other hand there is a report that the expression of epidermal growth factor receptor (EGF-R) at keratinocyte is accelerated at the affected part [J. Dermatol. Sci., 16, 120–128 (1998)]. While the expression of EGF-R in keratinocyte is normally induced by stimulation with interleukin-6 (IL-6), EGF-R was expressed at keratinocyte of psoriasis irrrespective of existence or absence of IL-6 stimulation.

The promoter region of EGF-R gene contains an abundance of CpG sequence and it was shown that transcription factors bind to the region [J. Biol. Chem., 266, 1746–1753 (1991), J. Biol. Chem., 263, 5693–5699 (1988)].

The sequence of the promoter region of human EGF-R gene is disclosed in accession number M38425 of GenBank database. THE CpG sequence is especially abundant and the binding sequences of transcription actor are scattered in the region about 500 bases upstream from the translation initiation point ($1114^{th}$) and the region about 800 bases downstream from the initiation point of the $1^{st}$ intron in the base sequence [J. Biol. Chem., 266, 1746–1753 (1991), J. Biol. Chem., 263, 5693–5699 (1988)].

Conventional diagnosis of psoriasis has been mostly performed by long time observation by dermatologists according to the diagnostic standard (PASI: psoriasis area and severity index) described in Dermatologica, 157, 238–244 (1978), J. Dermatol. Sci., 16, 165–169 (1998) and the like. Such diagnosis needs experienced dermatologists, and long time and much work or observing tissue lesions and symptoms. Therefore a speedy, reliable and reproducible diagnostic method has been desired.

Chronic rheumatoid arthritis is one of systemic autoimmune diseases and a cell-proliferating disease accompanying abnormal proliferation and inflammation of arthrosynovial cedes [Nippon Rinsho, 57, 333–338 (1999)]. The cause of chronic rheumatoid arthritis is yet to be solved. Although families with high incidence of chronic rheumatoid arthritis are known and the correlation with genotype of human histocompatibility antigen gene HLA-DR4 has been suggested, the cause itself is not yet known. There is a report that the activity of epidermal growth factor-like receptor 2 (erbB2/HER2/neu) is increased at the affected part [Seminars in Arthritis & Rheumatism, 21, 317–329 (1992)].

The sequence of the promoter region of human epidermal growth factor-like receptor 2 (erbB2/HER2/neu) gene is disclosed in accession number Z13970 of GenBank database. The region contains an abundance of CpG sequence and transcription factor Sp1 is suggested to bind to the region [Mol. Cell. Biol., 7, 2597–2601 (1987), Proc. Natl. Acad. Sci. USA, 84, 4374–4378 (1987), J. Biol. Chem., 265, 4389–4393 (1990), Gene 136, 361–364 (1993), Cancer Res., 54, 4193–4199 (1994)].

Conventional diagnosis of chronic rheumatoid arthritis has been performed by long time observation by specialized medical doctors according to the diagnosis standard described in [Arthritis Reum., 31, 315–324 (1988)] and the like. Such diagnosis needs experienced medical doctors, and long time and much work for observing tissue legions and symptoms. Therefore a speedy, reliable and reproducible diagnostic method has been desired.

DISCLOSURE OF THE INVENTION

The invention is to provide a speedy, reliable,and reproducible method for diagnosing cell-proliferating diseases.

The invention relates to below mentioned (1)–(16).

(1) A diagnostic method for detecting cell-proliferating diseases characterized by determining the methylation level of cytosine residues at the specific region of genome DNA involved in the expression of cytokine receptor gene.

(2) A diagnostic method described in (1) wherein the cytokine receptor gene is the gene of a receptor selected from tyrosine kinase receptor family, serine-threonine kinase receptor family, interleukin receptor family, interferon receptor family, immunoglobulin receptor family, apoptotic receptor family and seven transmembrane receptor family.

(3) A diagnostic method described in (2) wherein the tyrosine kinase receptor gene is the gene of a receptor selected from epidermal growth factor receptor, epidermal growth factor-like receptor 2 (erbB2/HER2/neu), platelet derived growth factor receptor and vascular endothelial cell growth factor receptor.

(4) A diagnostic method described in (1) wherein the cell-proliferating disease is a cell-proliferating disease selected from psoriasis, chronic rheumatoid arthritis, arteriosclerosis, restenosis, diabetic retinopathy, retinopathy of prematurity and solid tumor.

(5) A diagnostic method described in (1) wherein the specific region is a region in CpG island of promoter or intron.

(6) A diagnostic method described in (1) wherein the specific region is a region involved in the expression of epidermal growth factor receptor gene and a region represented by the nucleotide sequence from $381^{st}$ position to $962^{nd}$ position in the nucleotide sequence as described in Seq. ID No. 4.

(7) A diagnostic method described in (6) characterized by determining the methylation level of $668^{th}$, $671^{st}$, $687^{th}$ and $697^{th}$ cytosine residues in the nucleotide sequence as described in Seq. ID No. 4.

(8) A diagnostic method described in (7) characterized by analyzing the methylation level of $668^{th}$ cytosine residue in the nucleotide sequence as described in Seq. ID No; 4.

(9) A DNA primer having nucleotide sequence represented by Seq. ID No. 1 or 2 used for diagnostic method described in any one of (1) to (8).

(10) A diagnostic method described in (1) wherein the specific region is the region involved in the expression of epidermal growth factor-like receptor 2 (erbB2/HER2/neu) and represented by nucleotide sequence of Seq. ID No. 8.

(11) A diagnostic method described in (10) characterized by determining the methylation level of $268^{th}$, $276^{th}$ and $288^{th}$ cytosine residues in the nucleotide sequence as described in Seq. ID No. 8.

(12) A diagnostic method described in (11) characterized by analyzing the methylation level of $268^{th}$ cytosine residue in the nucleotide sequence as described in Seq. ID No. 8.

(13) A DNA primer having nucleotide sequence represented by Seq. ID No. 5 or 6 used for any one of diagnostic methods described in (1) to (4) and (10) to (12).

(14) A DNA having nucleotide sequence represented by Seq. ID No. 1, 2, 5 or 6.

(15) A method of detecting the methylation level of cytosine residue(s) in the specific region of DNA involved in the expression of cytokine receptor gene.

(16) A method described in (15) wherein the method of detecting the methylation level is A method using methylation sensitive restriction enzyme, a method using chemical modification by hydrazine, permanganic acids or sodium bisulfite, an immunological method using antibodies specific to methylated DNA, affinity column chromatography method or DGGE (denaturing gradient gel electrophoresis) method.

This invention relates to a diagnostic method for detecting cell-proliferating diseases characterized by determining the methylation level of cytosine residues at the specific region of genome DNA involved in the expression of cytokine receptor gene.

Cytokine is a general term for protein cell-cell signal transduction molecules, which regulate proliferation or differentiation of animal cells.

Examples of cytokine receptors include tyrosine kinase receptor family, serine-threonine kinase receptor family, interleukin receptor family, interferon receptor family, immunoglobulin receptor family, apoptotic receptor family and seven transmembrane receptor family.

Examples of tyrosine kinase receptor family include epidermal growth factor-receptor (hereinafter "EGF-R") [J. Biol. Chem., 266, 1746–1753 (1991), J. Biol. Chem., 263, 5693–5699 (1988)], epidermal cell growth factor-like receptor 2 (erbB2/HER2/neu) [Biochim. Biophys. Acta, 1377, M25–M37 (1998), Biochim. Biohpys. Acta, 1198, 165–184 (1994), Molec. Cell. Biol., 7, 2597–2601 (1987)], platelet derived growth factor-receptor (hereinafter "PDGF-R") [J. Biol. Chem., 269, 32023–32026 (1994), Oncogene, 10, 1667–1672 (1995)], vascular endothelial growth factor-receptor (hereinafter "VEGF-R") [J. Biol. Chem., 270, 27948–27953 (1995)].

Examples of the region involved in the expression of the above-mentioned receptor genes include the region from $-152^{nd}$ nucleotide to $-733^{rd}$ nucleotide upstream from translation initiation point of EGF-R gene, the region from $-1^{st}$ to $-647^{th}$ nucleotide upstream from translation initiation point of erbB2/HER2/neu gene [Mol. Cell. Biol., 7, 2597–2601 (1987)], the region from $-1^{st}$ to $-2060^{th}$ nucleotide upstream from transcription initiation point of PDGF-R gene [Oncogene, 10, 1667–1672 (1995)], the region from $-720^{th}$ to $+548^{th}$ nucleotide around transcription initiation point of VEGF-R gene [J. Biol. Chem., 270, 27948–27953 (1995)] and the like.

Cell-proliferating diseases are diseases like psoriasis characterized by keratin hypertrophy accompanying proliferation of epidermal cells and abnormal keratinization, chronic rheumatoid arthritis characterized by proliferation of synovial cell and villus hypertrophy, arteriosclerosis and restenosis characterized by proliferation of arterial smooth muscle cells and vascular media hypertropby, diabetic retinopathy, retinopathy of prematurity and solid tumor characterized by proliferation of vascular endothelial cells and vascularization, and the like.

The diagnostic method is described referring to psoriasis as an example in the following.

Genome DNAs of a person to be diagnosed are collected from samples such as blood, saliva, sperm, skin tiasue, tissue used for biopsy and the like respectively.

As methods or collecting genome DNAs from samples, a method described in Proc. Natl. Acad. Sci. USA, 74, 1245–1249 (1977), a method using ReadyAmp™ Genomic DNA Purification System (Promega) and the like are used.

As methods for determining the methylation level of genome DNAs obtained in the above, a method using methylation sensitive restriction enzyme described in Nucleic Acids Res., 26, 2255–2264 (1998), a method using chemical modification by hydrazine, permanganic acids or sodium bisulfite, an immunological method using antibodies specific to methylated DNA, affinity column chromatography method using MBD (methyl-CpG binding domain) such as MeCP2 and DGGE (denaturing gradient gel electrophoresis) method [Proc. Natl. Acad. Sci. USA, 96, 2913–2018 (1999)] and the like are used. An example is described below.

According to Proc. Natl. Acad. Sci. USA, 89, 1827–1831 (1992), the genome DNA is treated by sodium bisulfite, by which treatment cytosine residues are deaminated into uracil residues while methylated cytosine residues remain as they are.

Primers are designed to amplify the region involved in EGF-R gene expression by polymerase chain reaction (PCR). The primers are designed by hypothesizing a nudeotide sequence where cytosine is replaced by uracil in the region to be amplified. As the region to be amplified, a part with an abundance of CpG nucleotide sequence is preferable. In EGF-R gene, the promoter region is a preferable example. The example is the sequence from $381^{st}$ nucleotide to $962^{nd}$ nucleotide in the nucleotide sequence as described in Seq. ID No. 4. $1114^{th}$ nucleotide in the nucleotide sequence as described Seq. ID No. 4 corresponds to the translation initiation point of EGF-R, and the region from $-152^{nd}$ nucleotide to $-733^{rd}$ nucleotide upstream therefrom corresponds to the promoter region. Any primer is feasible if it is designed based on the part of nucleotide sequence to be amplified. The examples are nucleotide sequences represented by Seq. ID No. 1 and Seq. ID No. 2.

When PCR is performed with the above-mentioned primer, methylated cytosine residues are amplified as cytosines, while unmethylated cytosine residues are amplified as thymine residues. Therefore, the methylation level of cytosine residues in original genome is determined by decoding nucleotide sequence of DNA amplified by said PCR (hereinafter "PCR product").

Decoding nucleotide sequence of said PCR product is carried out as follows:

Firstly said PCR product is fractionated, extracted and purified by agarose gel electrophoresis and the like described in J. Sambrook, E. F. Fritsch, T. Maniatis, Molecular Cloning a Laboratory Manual $2^{nd}$ Ed., Cold Spring Harbor Laboratory Press (1989) (hereinafter "Molecular Cloning $2^{nd}$ Ed.").

Then nucleotide sequence determination reaction is performed by using said PCR product as template DNA, primer represented by Seq. ID No. 2, DNA polymerase and dideoxynucleotide. The nucleotide sequence determination reaction is performed by polymerizing nucleotide by DNA polymerase in the presence of dideoxynucleotide. Examples include a method of polymerizing RI-labeled nucleotide as described in Molecular Cloning $2^{nd}$ Ed. and a method of polymerizing fluorescence-labeled nucleotide by Dye Terminator Cycle Sequencing Kit of Perkin Elmer and Thermal Cycler™ of PerkinElmer.

As methods for decoding nucleotide sequence of the sample after the sequence determination reaction, the method by subjecting the reaction sample having incorporated RI-labeled nucleotide to denatured polyacrylamide gel electrophoresis followed by autoradiography (Molecular Cloning $2^{nd}$ Ed.), or the method by subjecting the reaction sample having incorporated fluorescence-labeled nucleotide to automatic nucleotide sequence decoding apparatus like PRISM™ 310 Genetic Analyzer (PE Applied Biotechnologies), and the like.

When nucleotide sequence of PCR product is decoded by the above-mentioned process, in the region of genome DNA where cytosine residue(s) is methylated, the signal(s) indicated by autoradiography or automatic nucleotide sequence decoding apparatus is only a peak(s) of cytosine, while in the region where unmethylated, the signal(s) is only a peak(s) of thymine. However where partially methylated, the signal is a mixture of cytosine and thymine.

To further investigate the methylation level, said PCR product is cloned in a suitable vector and nucleotide sequences of several clones are decoded.

Examples of cloning vectors are plasmid vectors like pUC19 and pBlueScript SK(-) (Stratagene), and phage vectors like M13mp19 and λgt11.

Cloning is performed according to a method described in Molecular Cloning $2^{nd}$ Ed. PCR product is inserted and connected into a vector. The vector is transformed into host E. coli like JM109 strain and DH5 α strain, and colonies are selected. E. coli of each colony is cultivated and each cloned DNA is extracted and purified.

Nucleotide sequences of thus cloned DNAs are decoded by the method mentioned above. The sequence determination reaction is performed using each of cloned DNAs as template and the nucleotide sequence of reaction sample is decoded by autoradiography or automatic nucleotide sequence decoding apparatus.

Methylation pattern of cytosine residue(s) is analyzed after decoding nucleotide sequence. Specifically, $-446^{th}$, $-443^{rd}$, $-427^{th}$ and $-417^{th}$ cytosine residues (corresponding to $668^{th}$, $671^{st}$, $687^{th}$ and $697^{th}$ positions in the nucleotide sequence as described in Seq. ID No. 4) counted from the translation initiation point of EGF-R gene (corresponding to nucleotide number $1114^{th}$ in the nucleotide sequence as described in Seq. ID No. 4) are analyzed. As understood from the result of diagnosis of 30 patients and 30 healthy people shown in Table 1 of Example 1(10), when the number of methylated residues among 4 residues is not more than 2, the person is diagnosed as psoriasis at the probability of about 83% (25/30). The probability of mistaking healthy person for a patient is about 13%(4/30). When $-446^{th}$ cytosine residue is not methylated, the person of sample is diagnosed as psoriasis at a probability of about 83%(25/30) as shown in Example 1(11). The probability of mistaking healthy person for a patient is about 33%(10/30).

Diagnosis of chronic rheumatoid arthritis is performed in a similar way as diagnosis of psoriasis descried in the above. As understood form the result of diagnosis of 9 patients and 3 healthy people shown in Table 2 of Example 2(9), when the total number of methylated residues among $-380^{th}$, $-372^{nd}$ and $-360^{th}$ cytosine residues (corresponding to $268^{th}$, $276^{th}$ and $288^{th}$ positions in the nucleotide sequence as described in Seq. ID No. 8) upstream from translation initiation point of erbB2 gene is not more than 1, the person of sample is diagnosed as chronic rheumatoid arthritis. The probability of mistaking healthy person for a patient is about 33%(1/3). When $-380^{th}$ cytosine residue (corresponding to $268^{th}$ position in the nucleotide sequence as described in Seq. ID No. 8) is not methylated, the person of sample is diagnosed as chronic rheumatoid arthritis at a probability of about 67%(6/9) as shown in Example 2(10).

BRIEF DESCRIPTION OF THE DRAWINGS

FIG. 1 shows the state of methylation of $-446^{th}$, $-443^{rd}$, $-427^{th}$ and $-417^{th}$ cytosine residues (corresponding to $668^{th}$, $671^{st}$, $687^{th}$ and $697^{th}$ positions in the nucleotide sequence as described in Seq. ID No. 4) from translation initiation point ($1114^{th}$ position in the nucleotide sequence as described in Seq. ID No. 4) of EGF-R genome DNA. N1 to N30 indicates subjects of healthy people and P1 to P30 indicates subjects of psoriasis respectively. Most frequently detected methylation pattern among 20 clones, nucleotide sequences of which were analyzed, is shown as a representative. The case where cytosine residue is methylated is shown by black spot (●).

FIG. 2 shows the state of methylation of $-380^{th}$, $-372^{nd}$ and $-360^{th}$ cytosine residues (corresponding to $268^{th}$, $276^{th}$ and $288^{th}$ positions in the nucleotide sequence as described in Seq. ID No. 8) upstream from translation initiation point, in the methylation pattern of cytosines in the promoter region of erbB2 gene of genome DNA of samples, obtained as a result of Example 2(7). C1 to C3 indicates 3 subjects of healthy people and R1 to R9 indicates 9 subjects of chronic rheumatoid arthritis respectively. Most frequently detected methylation pattern among 20 clones, nucleotide sequences of which were analyzed, is shown as a representative. The case where cytosine residue is methylated is shown by black spot (●).

BEST MODE TO WORK THE INVENTION

Example 1
(1) Selection of Trial Subjects

Contraction/non-contraction and the degree of psoriasis with trial subjects were diagnosed by specialized doctors according to the international diagnosis standard (PASI) [Dermatologica, 157, 238–244 (1978), J. Dermatol. Sci., 16, 165–169 (1998)]. Thirty (30) patients diagnosed as psoriasis and 30 healthy people were selected as trial subjects.
(2) Collection of Genome DNA from Trial Subjects 0.4 ml venous blood was taken from the, upper arm of each trial subject. DNA was extracted from the blood and purified. Extraction and purification of the DNA were performed by ReadyAmp™ Genomic Purification System (Promega) according to the attached manual. Purified DNA was dissolved in TE buffer (10 mM Tris hydrochloride, 1 mM EDTA, pH8.0) to make the final concentration at 100 μg/ml. Thus obtained materials were used as genome DNA.
(3) Sodium Bisulfite Treatment of Genome DNA According to a method described in Proc. Natl. Acad. Sci. USA, 89, 1827–1832 (1992), each genome DNA obtained in Example 1(2) was treated with sodium bisulfite.

A mixture of 1 μg of genome DNA sample and 9 μg of pBlueScript SK(-) plasmid DNA (Stratagene) as a carrier DNA was incubated in 50 μl of 0.25M sodium hydroxide aqueous solution at 37° C. for 10 minutes to be denatured. Thus denatured mixture was mixed with 520 μl of 3.6M sodium bisulfite aqueous solution (pH5.0) and 30 μl of 10 mM hydroquinone aqueous solution and incubated at 50° C. for 16 hours.

Thus obtained DNA was purified with Wizard Genomic DNA Purification System (Promege) according to the attached manual and the purified DNA was eluted with 50 μl of TE buffer solution (10 mM Tris hydrochloride, 1 mM EDTA, pH8.0). Eluted DNA was mixed with 5 μl of 2N sodium hydroxide and incubated at a room temperature for 5 minutes. The mixture was mixed/stirred with 100 μl of 100% ethanol and kept at −20° C. for 30 minutes. Then the mixture was centrifuged at 10,000×g for 10 minutes to isolate the precipitate. Thus isolated precipitate was suspended in 100 μl of 70% ethanol. The suspension was centrifuged at 10,000×g for 5 minutes to isolate precipitate. Thus isolated precipitate was dried in vacuum and dissolved in 50 μl of pure water to prepare DNA sample treated with sodium bisulfite.
(4) Design and Synthesis of PCR Primer The methylation level of cytosine residues of CpG sequence abundant in the region around the promoter of human epidermal growth factor receptor (EGF-R) gene was analyzed. The region around the promoter of EGF-R gene means the region from $-152^{nd}$ nucleotide to $-733^{rd}$ nucleotide upstream form translation initiation point of EGF-R gene, which corresponds to nucleotide sequence from $381^{st}$ position to $962^{nd}$ position in the nucleotide sequence as described in Seq. ID No. 4. MP3 (Seq. ID No. 1) and MP4 (Seq. ID No. 2), which are PCR primers for analyzing methylation of cytosine residues of said region, were designed as follows.

Unmethylated cytosine residues are altered to uracil residues by sodium bisulfite treatment described in Example 1(3). Therefore they become thymine residues by subsequent PCR amplification. Seq. ID No. 3 was first designed by hypothesizing the sequence of the region where cytosine residues (C) are replaced by thymine residues (T). MP4 primer (Seq. ID No. 2) is a sense primer corresponding to the nucleotide sequence from $1^{st}$ position to $32^{nd}$ position in Seq. ID No. 3, in which an incision sequence of restriction enzyme HindIII (AAGCTT) has been introduced into around 5' terminal (from $7^{th}$ nucleotide to $12^{th}$ nucleotide in Seq. ID No. 2) to make the subsequent cloning step easy.

MP3 primer (Seq. ID No. 1) is an antisense primer corresponding to the part from $553^{th}$ nucleotide to $582^{nd}$ nucleotide in Seq. ID No. 3, in which an incision sequence of restriction enzyme EcoRI (GAATTC) has been introduced into around 5' terminal (from $8^{th}$ nucleotide to $13^{th}$ nucleotide in Seq. ID No. 1) to make the subsequence cloning step easy.

Above-mentioned primers were prepared by chemical synthesis of oligonucleotide.
(5) Amplification by PCR Following PCR was performed by using as template each DNA sample treated by sodium bisulfite (30 derived from patients and 30 derived from healthy people) described in Example 1(3) with MP3 primer and MP4 primer.

Each 1 μl of template DNA was mixed with 35.5 μl of pure water, 5 μl of 10×PCR buffer containing magnesium chloride (GIBCO BRL), 1 μl of 10 mM dNTP mix (GIBCO BRL) and 2.5 μl of dimethylsulfoxide (DMSO; Sigma). It was further mixed with 2.5 μl of MP3 primer and MP4 primer solutions in pure water at a concentration of 20 μM each. The mixture (50 μl) was heated at 95° C. for 5 minutes and mixed with 1 unit of Taq DNA polymerese (GIBCO BRL). PCR of 35 cycles was performed using Thermal Cycler™ of PerkinElmer with a program of at 96° C. for 45 seconds, at 53° C. for 30 seconds, at 72° C. for 1 minute.
(6) Purification of PCR Product Each PCR product obtained in Example 1(5) was fractionated by low melting point agarose gel electrophoresis according to a method described in Molecular Cloning $2^{nd}$ Ed. After staining said low melting point agarose gel with ethidium bromide, the part of 582 bp (base pair) band of low melting point agarose gel was excised under radiation of ultraviolet light. DNA of the excised band was purified by Wizard PCR Preps DNA Purification System (Promega)

according to the attached manual and the purified DNA was eluted with 50 µl of TE buffer (10 mM Tris hydrochloride, 1 mM EDTA, pH8.0) to obtain purified PCR product.

(7) Direct determination of Nucleotide Sequence of PCR Product

Nucleotide sequences of purified PCR products obtained in Example 1(6) were determined.

Firstly sequence determination reaction was performed by Dye Terminator Cycle Sequencing Kit (Perkin Elmer) and Thermal Cycler™ (PerkinElmer), using purified PCR product as template and MP4 primer. During the sequence determination reaction fluorescence-labeled nucleotide was incorporated. The reaction was performed according to the attached manual.

Then nucleotide sequence of each reaction sample was decoded by using automatic nucleotide sequence decoding apparatus PRISM™ 310 Genetic Analyzer (PE Applied Biotechnologies) according to the attached manual.

The methylation level of cytosine residues in genome DNA samples taken from each trial subject was determined from the decoded nucleotide sequence. Where cytosine was methylated, signals of automatic nucleotide sequence decoding apparatus were peaks only of cytosine, while where not methylated, signals were only peaks of thymine. However where partially methylated, signals were mixtures of cytosine and thymine.

To further investigate the methylation level, said PCR product was cloned in a vector and nucleotide sequences of several clones were decoded.

(8) Cloning of PCR Product and Determination of Nucleotide Sequence

To 10 µl of purified PCR product obtained in Example 1(6), 1 µl of react buffer 2 (GIBCO BRL), 1 unit of restriction enzyme EcoRI (GIBCO BRL) and 1 unit of HindIII (GIBCO BRL) was added, and reacted at 37° C. for 1 hour to cleave DNA of purified PCR product. The DNA was mixed/stirred with 100 µl of 100% ethanol kept at −20° C. for 30 minutes and centrifuged at 10,000×g for 10 minutes to obtain precipitate. The precipitate was suspended in 100 µl of 70% ethanol and centrifuged at 10,000×g for 5 minutes to obtain precipitate. The precipitate was dried under vacuum and dissolved in 20 µl of pure water to prepare EcoRI-HindIII cleavage DNA fragment.

In a similar manner 0.5 µg of pBlueScript SK(−)plasmid DNA (Stratagene) was cleaved by restriction enzymes EcoRI and HindIII, DNA fragment of about 2.7 kbp was fractionated by low melting point agarose gel electrophoresis described in Molecular Cloning $2^{nd}$ Ed., the fractionated DNA was purified with Wizard PCR Preps DNA Purification System (Promega) according to the attached manual and the purified DNA was eluted by 50 µl of TE buffer (10 mM Tris hydrochloride, 1 mM EDTA, pH8.0) to prepare EcoRI-HindIII cleavage vector DNA fragment.

1 µl of thus obtained EcoRI-HindIII cleavage DNA fragment and 0.5 µl of EcoRI-HindIII cleavage vector DNA fragment were mixed. The mixture was mixed with 6 µl of pure water, 2 µl of buffer for T4DNA ligase (GIBCO BRL) and 1 unit of T4DNA ligase (GIBCO BRL), and kept at 16° C. for 16 hours to perform DNA ligation reaction.

Each DNA ligation reaction product was transformed into E. coli JM109 strain according to the method described in Molecular Cloning $2^{nd}$ Ed. Transformed E. coli JM109 strain was cultured on LB plate agar medium (Molecular Cloning $2^{nd}$ Ed.) containing 50 µg/ml of ampicillin (Sigma), 40 µg/ml of isopropylthio-β-D-galactoside (Sigma) and 40 µg/ml of X-gal (Sigma) at 37° C. for 1 day. Twenty (20) white colonies were randomly selected from colonies appeared on each plate agar medium and plasmid DNA from each colony was prepared according to Molecular Cloning $2^{nd}$ Ed.

Using each plasmid DNA as template, universal primer as primer and Dye Terminator Cycle Sequencing Kit (Perkin Elmer) and Thermal Cycler™ (PerkinElmer), the sequence determination reaction was performed, during which reaction fluorescence-labeled nucleotide was incorporated. The reaction was manipulated according to the attached manual. Nucleotide sequence of each reaction sample was decoded by automatic nucleotide sequence decoding apparatus PRISM™ 310 Genetic Analyzer (PE Applied Biotechnologies) according to the attached manual.

The methylation patterns of cytosine residues of genome DNA samples taken from each of trial subjects were determined from the result of decoding.

(9) State of Methylation of Cytosine Residues

Based on the results of Example 1(7) and 1(8), as for methylation pattern of the promoter region of EGF-R gene of genome DNA of trial subjects, methylation of $-446^{th}$, $-443^{rd}$, $-427^{th}$ and $-417^{th}$ cytosine residues ($668^{th}$, $671^{st}$, $687^{th}$ and $697^{th}$ position in the nucleotide sequence as described in Seq. ID No. 4) is shown in FIG. 1. N1 to N30 indicates 30 subjects of healthy people and P1 to P30 indicates 30 subjects of psoriasis patients. Methylation pattern which is most frequently detected in 20 clones, sequences of which were decoded, is shown as a representative. The case where cytosine residue was methylated is represented by black spot (●) while the case where not methylated is left blank.

(10) Diagnostic Method for Psoriasis (No. 1)

The number of methylated cytosine residues among four of $-446^{th}$, $-443^{rd}$, $-427^{th}$ and $-417^{th}$ cytosine residues from transcription initiation point of EGF-R gene was counted. For example, four were found in N1, three in N2, one in P1 and zero in P2. The frequency distribution is tabled in groups of patients and healthy people respetively.

TABLE 1

| Number of methylated residue | 0 | 1 | 2 | 3 | 4 |
|---|---|---|---|---|---|
| Healthy people | 1 | 0 | 3 | 16 | 10 |
| Patients | 15 | 7 | 3 | 5 | 0 |

When diagnosis standard is set at the point that the number of methylated residue is not more than 1, psoriasis is diagnosed at a probability of about 73% (22/30). The probability of mistaking a healthy person for a patient is about 3% (1/30).

When diagnosis standard is act at the point that the number of methylated residue is not more than 2, psoriasis is diagnosed at a probability of about 83% (25/30). The probability of mistaking a healthy person for a patient is about 13% (4/30).

(11) Diagnosis Method for Psoriasis (No. 2)

$446^{th}$ cytosine residue is focused on. The residue is methylated in 5 patients and in 20 healthy people. Therefore, when the residue is not methylated, it is diagnosed to be psoriasis at a probability of about 83% (25/30). The probability of mistaking a healthy person for a patient is about 33% (10/30).

Example 2

(1) Selection of Trial Subjects

Contraction/non-contraction and the degree of chronic rheumatoid arthritis with trial subjects were diagnosed by specialized doctors according to the diagnosis standard of American Rheumatoid Academy [Arthritis Reum., 31, 315–324 (1988)]. Nine (9) patients diagnosed as chronic rheumatoid arthritis and 3 healthy people were selected as trial subjects.

(2) Collection of Genome DNA from Trial Subjects 0.4 ml venous blood was taken from the upper arm of each trial subject of Example 2(1). DNA was extracted from the taken blood and purified. Extraction and purification of the DNA was performed by ReadyAmp™ Genomic DNA Purification System (Promega) according to the attached manual. Purified DNA was dissolved in TE buffer (10 mM Tris hydrochloride, 1 mM EDTA, pH8.0) to make the final concentration at 100 µg/ml. Thus obtained materials were used as genome DNA.

(3) Sodium Bisulfite Treatment of Genome DNA Samples

According to a method described in Proc. Natl. Acad. Sci. USA, 89, 1827–1832 (1992) each genome DNA obtained in Example 2(2) was treated with sodium bisulfite. A mixture of 1 µg of genome DNA and 9 µg of pBlueScript SK(-) plasmid DNA (Stratagene) as a carrier DNA was added to 50 µl of 0.25M sodium hydroxide aqueous solution and incubated at 37° C. for 10 minutes to be denatured. Thus denatured mixture was mixed with 520 µl of 3.6M sodium bisulfite aqueous solution (pH5.0) and 30 µl of 10 mM hydroquinone aqueous solution and incubated at 50° C. for 16 hours.

Thus obtained DNA was purified with Wizard Genomic DNA Purification System (Promega) according to the attached manual and the purified DNA was eluted with 50 µl of TE buffer solution (10 mM Tris hydrochloride, 1 mM EDTA, ph8.0). Eluted DNA was mixed with 5 µl of 2N sodium hydroxide and incubated at a room temperature for 5 minutes. The mixture was mixed/stirred with 100 µl of 100% ethanol and kept at –20° C. for 30 minutes. Then the mixture was centrifuged at 10,000×g for 10 minutes to isolate the precipitate. Thus obtained precipitate was suspended in 100 µl of 70% ethanol. The suspension was subjected to centrifugation at 10,000×g for 5 minutes to obtain precipitate. Thus obtained precipitate was dried in vacuum and dissolved in 50 µl of pure water to prepare DNA sample treated with sodium bisulfite.

(4) Design and Synthesis of PCR Primer

The methylation level of cytosine residues of CpG sequence abundant in the region around the promoter of human epidermal growth factor-like receptor 2 (erbB2/HER2/neu) gene (hereinafter "erbB2 gene") was analyzed. The region around the promoter of erbB2 gene means the region around the nucleotide sequence from $-1^{st}$ position to $-647^{th}$ position upstream from translation initiation point of erbB2 gene, concretely describing, the region around the nucleotide equence represented by Seq. ID No. 8 [Mol. Cell. Biol., 7, 2597–2601 (1987), Gene 136, 361–364 (1993)]. This corresponds to the nucleotide sequence from $3001^{st}$ position to $3647^{th}$ position in the nucleotide sequence represented by accession number Z13970 of GenBank database. In Seq. ID No. 8, the nucleotide sequence from $87^{th}$ position to $449^{th}$ position was focused on in this example. This region corresponds to the nucleotide sequence from $-199^{th}$ to $-561^{st}$ upstream from translation initiation point. NeuS (Seq. ID No. 5) and NeuA (Seq. ID No. 6), which are PCR primers for analyzing methylation of cytosine residues of said region, were designed as follows.

Seq. ID No. 7 was designed by hypothesizing the nucleotide sequence where cytosine residues (C) in the region (nucleotide sequence from $87^{th}$ position to $449^{th}$ position in Seq. ID No. 8) were replaced by thymine residues (T), because unmethylated cytosine residues are thought to be altered to uracil residues by sodium bisulfite treatment described in Example 2(3) and nucleotide sequences after PCR amplification are thought to be altered to thymine residues.

NeuS primer (Seq. ID No. 5) is a sense primer corresponding to the nucleotide sequence from $1^{st}$ position to $25^{th}$ position of Seq. ID No. 7. NeuA primer (Seq. ID No. 6) is an antisense primer corresponding to the nucleotide sequence from $339^{th}$ to $363^{rd}$ of Seq. ID No. 7. Chemical synthesis of those primer oligonucleotides was performed by Phosphoramidite method [S. L. Beaucage & M. H. Caruthers, Tetrahedron Letters, 22 1859 (1981)].

(5) Amplification by PCR

Using each DNA sample treated with sodium bisulfite described in Example 2(3) as template DNA (9 derived from patients and 3 derived from healthy people) and NeuS primer and NeuA primer, PCR was performed as follows:

Each 1 µl of template DNA was mixed with 35.5 µl of pure water, 5 µl of 10×PCR buffer containing magnesium chloride (GIBCO BRL), 1 µl of 10 mMdNTP mix (GIBCO BRL) and 2.5 µl of dimethylsulfoxide (DMSO; Sigma). It was further mixed with each 2.5 µl of NeuS primer and NeuA primer dissolved in pure water at a concentration of 20 µM. The mixture (50 µl) was heated at 95° C. for 5 minutes and mixed with 1 unit of Taq DNA polymerase (GIBCO BRL). PCR of 40 cycles was performed using Thermal Cycler™ of PerkinElmer with a program of at 94° C. for 30 seconds, at 53° C. for 30 seconds, at 72° C. for 1 minute.

(6) Purification of PCR Product

Each PCR product obtained in Example 2(5) (9 samples collected from patients and 3 samples collected from healthy people) was fractionated by low melting point agarose gel electrophoresis according to the method described in Molecular Cloning $2^{nd}$ Ed. After staining said low melting point agarose gel with ethidium bromide, the part of 363 bp (base pair) band of low melting point agaose gel was excised under radiation of ultraviolet light. DNA of the excised part was purified by Wizard PCR Preps DNA Purification System (Promega) according to the attached manual and the purified DNA was eluted with 50 µl of TE buffer (10 mM Tris hydrochloride, 1 mM EDTA, pH8.0) to obtain purified PCR product.

(7) Cloning of PCR Product and Nucleotide Sequence Determination

Each 10 µl of purified PCR products obtained in Example 2(6) (9 samples collected from patients and 3 samples collected from healthy people) was subjected to cloning by using commercially available TA cloning kit pGEM-T Easy Vector System II (Promega) according to the attached protocol (Promega Protocol TM042). Finally transformed *E. coli* JM109 strain (attached to the kit) was cultured on LB plate agar medium (Molecular Cloning $2^{nd}$ Ed.) containing 50 µg/ml of ampicillin (Sigma), 40 µg/ml of isopropylthio-β-D-galactoside (Sigma) and 40 µg/ml of X-gal (Sigma) at 37° C. for 1 day. Twenty (20) white colonies were randomly selected from colonies appeared on each plate agar medium and plasmid DNA was prepared from each colony according to Molecular Cloning $2^{nd}$ Ed.

Using each plasmid DNA as template, Universal Primer as primer and Dye Terminator Cycle Sequencing Kit (Perkin Elmer) and Thermal Cycler™ (PerkinElmer), sequence determination reaction was performed, during which reaction fluorescence-labeled nucleotide was incorporated. The reaction was manipulated according to the manual attached to the kit. Nucleotide sequence of each reaction sample was decoded by automatic nucleotide sequence decoding apparatus PRISM™ 310 Genetic Analyzer (PE Applied Biotechnologies) according to the manual attached to the apparatus.

The methylation patterns of cytosine residues in genome DNA samples taken from trial subjects were determined from the results of decoding. Namely, cytosine methylated in genome was read as cytosine by the automatic nucleotide sequence decoding apparatus, while unmethylated cytosine was read as thymine.

(8) State of Methylation of Cytosine Residues

Based on the results of Example 2(7), as for methylation pattern of promoter region of erbB2 gene of genome DNA of trial subjects, the state of methylation of $-380^{th}$, $-372^{nd}$ and $-360^{th}$ cytosine residues (corresponding to base number $268^{th}$, $276^{th}$ and $288^{th}$ position in the nucleotide sequence as described in Seq. ID No. 8) is shown in FIG. 2. C1 to C3 indicates 3 subjects of healthy people and R1 to R9 indicates 9 subjects of chronic rheumatoid arthritis patients. Methylation pattern which was most frequently detected in 20 clones, sequences of which were decoded, is shown as a representative. The case where cytosine residue was methylated is represented by black spot (●) while the case where not methylated is left blank.

(9) Diagnostic Method for Chronic Rheumatoid Arthritis (No. 1)

As to the number of methylated cytosine residues among $-380^{th}$, $-372^{nd}$ and $-360^{th}$ cytosine residues from transcription initiation point of erbB2 gene, the frequency distribution is tabled below in groups of patients and healthy people respectively.

TABLE 2

| Number of methylated residue | 0 | 1 | 2 |
|---|---|---|---|
| Healthy people | 0 | 1 | 2 |
| Patients | 6 | 3 | 0 |

When the number of methylated residue is not more than 1, chronic rheumatoid arthritis is diagnosed. The probability of mistaking a healthy person for a patient is about 33% (1/3).

(10) Diagnosis Method for Chronic Rheumatoid Arthritis (No. 2)

Cytosine residue at nucleotide number 268 is focused on. The residue was methylated in all 3 healthy people while in only 3 of 9 patients. Therefore, when the cytosine residue is not methylated, it is diagnosed to be chronic rheumatoid arthritis at a probability of about 67% (%).

INDUSTRIAL APPLICABILITY

A diagnostic method for detecting cell-proliferating diseases by extracting genome DNA from blood etc. of trial subject and analyzing the methylation level of cytosine residues of cell-proliferating factor receptor gene is provided.

What is claimed is:

1. A method of detecting a predisposition of an individual for developing psoriasis comprising:

a) collecting a genomic DNA from a patient suspected of having psoriasis;
   b) amplifying the genomic DNA using primers; and
   c) determining the methylation of cytosine residues in epidermal growth factor receptor at positions 668, 671, 687, 697 of SEQ ID NO. 4;

wherein the presence of not more than one methylated cytosine is indicative of the individual to a predisposition to psoriasis.

2. A method of claim 1 wherein the genomic DNA is collected from a blood sample of a patient suspected of having psoriasis.

3. A method of claim 1 or 2 wherein the method of detecting the methylation is a method using methylation sensitive restriction enzyme, a method using chemical modification by hydrazine, permanganic acids or sodium bisulfite, an immunological method using antibodies specific to methylated DNA, affinity column method or DGGE (denaturing gradient gel electrophoresis) method.

* * * * *